United States Patent
Katzir et al.

(10) Patent No.: US 10,296,702 B2
(45) Date of Patent: May 21, 2019

(54) METHOD OF PERFORMING METROLOGY OPERATIONS AND SYSTEM THEREOF

(71) Applicant: Applied Materials Israel Ltd., Rehovot (IL)

(72) Inventors: Ron Katzir, Tel Aviv (IL); Imry Kissos, Kiryat-Ono (IL); Lavi Jacov Shachar, Tel Aviv (IL); Amit Batikoff, Petach Tikva (IL); Shaul Cohen, Irus (IL); Noam Zac, Kfar Saba (IL)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 38 days.

(21) Appl. No.: 15/698,585

(22) Filed: Sep. 7, 2017

(65) Prior Publication Data

US 2018/0268099 A1    Sep. 20, 2018

Related U.S. Application Data

(63) Continuation-in-part of application No. 15/460,078, filed on Mar. 15, 2017, now Pat. No. 10,120,973.

(51) Int. Cl.
| | |
|---|---|
| *G06F 17/50* | (2006.01) |
| *G06T 7/00* | (2017.01) |
| *G06T 7/33* | (2017.01) |
| *G06T 3/00* | (2006.01) |
| *G06T 7/73* | (2017.01) |

(52) U.S. Cl.
CPC ........ *G06F 17/5081* (2013.01); *G06T 3/0068* (2013.01); *G06T 7/001* (2013.01); *G06T 7/0006* (2013.01); *G06T 7/337* (2017.01); *G06T 7/74* (2017.01); *G06T 2200/24* (2013.01); *G06T 2207/30148* (2013.01)

(58) Field of Classification Search
USPC ........................................................ 716/136
See application file for complete search history.

(56) References Cited

U.S. PATENT DOCUMENTS

| | | |
|---|---|---|
| 6,869,739 B1 | 3/2005 | Ausschnitt et al. |
| 7,207,017 B1 | 4/2007 | Tabery et al. |

(Continued)

FOREIGN PATENT DOCUMENTS

| | | |
|---|---|---|
| WO | 2014081897 A1 | 5/2014 |
| WO | 2015153872 A1 | 10/2015 |
| WO | 2016010776 A1 | 1/2016 |

*Primary Examiner* — Suresh Memula
(74) *Attorney, Agent, or Firm* — Lowenstein Sandler LLP

(57) ABSTRACT

There are provided system and method of performing metrology operations related to a specimen. The method comprises: generating an examination recipe in accordance with a metrology application, the examination recipe specifying one or more metrology objects and one or more metrology operations related to the metrology application; obtaining an image-based representation of the specimen and a design-based representation of the specimen; mapping between the design-based representation of at least first metrology object and the image-based representation of at least first metrology object; and performing at least first metrology operation of the one or more metrology operations according to the examination recipe using the mapping, the at least first metrology operation specified as related to the at least first metrology object and to be performed on at least the image-based representation of the specimen.

20 Claims, 7 Drawing Sheets

(56) References Cited

U.S. PATENT DOCUMENTS

| | | | |
|---|---|---|---|
| 8,283,630 B2 | 10/2012 | Miyamoto et al. | |
| 8,432,441 B2 | 4/2013 | Fang et al. | |
| 8,445,871 B2 | 5/2013 | Matsuoka et al. | |
| 9,041,795 B2 | 5/2015 | Fang et al. | |
| 9,100,553 B2 | 8/2015 | Fang et al. | |
| 9,251,581 B1 | 2/2016 | Chen et al. | |
| 9,282,293 B2 | 3/2016 | Fang et al. | |
| 2006/0288325 A1 | 12/2006 | Miyamoto et al. | |
| 2007/0280527 A1 | 12/2007 | Almogy et al. | |
| 2013/0204569 A1 | 8/2013 | Goren et al. | |
| 2015/0041649 A1 | 2/2015 | Wang | |
| 2015/0069232 A1 | 3/2015 | Lin et al. | |
| 2015/0146967 A1 | 5/2015 | Miyamoto et al. | |
| 2015/0162249 A1 | 6/2015 | Ausschnitt et al. | |
| 2015/0212019 A1 | 7/2015 | Shishido et al. | |
| 2015/0278426 A1* | 10/2015 | Ning | G06F 17/5072 716/53 |
| 2016/0283617 A1* | 9/2016 | Bailey | G06F 17/5009 |
| 2016/0349742 A1 | 12/2016 | Dalla-Torre et al. | |
| 2017/0219928 A1* | 8/2017 | Heo | G03F 7/70633 |
| 2018/0113387 A1* | 4/2018 | Xiao | G01N 21/9501 |

\* cited by examiner

METHOD OF PERFORMING METROLOGY OPERATIONS AND SYSTEM THEREOF

CROSS-REFERENCE TO RELATED APPLICATIONS

This application is a continuation-in-part of co-pending U.S. patent application Ser. No. 15/460,078, filed on Mar. 15, 2017, which is herein incorporated by reference.

TECHNICAL FIELD

The presently disclosed subject matter relates, in general, to the field of metrology of semiconductor fabrication, and more specifically, to methods and systems of performing metrology operations related to a specimen.

BACKGROUND

Current demands for high density and performance associated with ultra large scale integration of fabricated devices require submicron features, increased transistor and circuit speeds, and improved reliability. As semiconductor processes progress, pattern dimensions such as line width, and other types of critical dimensions, are continuously shrunken. Such demands require formation of device features with high precision and uniformity, which, in turn, necessitates careful monitoring of the fabrication process, including frequent and detailed inspections and metrology operations related to the devices while they are still in the form of semiconductor wafers.

The term "specimen" used in this specification should be expansively construed to cover any kind of wafer, masks, and other structures, combinations and/or parts thereof used for manufacturing semiconductor integrated circuits, magnetic heads, flat panel displays, and other semiconductor-fabricated articles.

Unless specifically stated otherwise, the term "examination" used in this specification should be expansively construed to cover any kind of detection and/or classification of defects in an object. Examination is provided by using non-destructive examination tools during or after manufacture of the object to be examined. By way of non-limiting example, the examination process can include scanning (in a single or in multiple scans), sampling, reviewing, measuring, classifying and/or other operations provided with regard to the object or parts thereof, using one or more examination tools. Likewise, examination can be provided prior to manufacture of the object to be examined and can include, for example, generating an examination recipe(s). It is noted that, unless specifically stated otherwise, the term "examination" or its derivatives used in this specification are not limited with respect to the size of the inspected area(s), to the speed or resolution of the scanning or to the type of examination tools. A variety of non-destructive examination tools includes, by way of non-limiting example, scanning electron microscopes (SEM), tunneling electron microscope (TEM), atomic force microscopes (AFM), optical tools, etc.

The examination process can include a plurality of examination steps. During the manufacturing process, the examination steps can be performed a multiplicity of times, for example after the manufacturing or processing of certain layers, or the like. Additionally or alternatively, each examination step can be repeated multiple times, for example for different wafer locations or for the same wafer locations with different examination settings.

By way of non-limiting example, run-time examination can employ a two-step procedure, e.g. inspection of a specimen followed by review of sampled defects. During the inspection step, the surface of a specimen or a part thereof (e.g. areas of interest, hot spots, etc.) is typically scanned at relatively high-speed and/or low-resolution. The captured inspection image is analyzed in order to detect defects and obtain locations and other inspection attributes thereof. At the review step the images of at least part of defects detected during the inspection phase are, typically, captured at relatively low speed and/or high-resolution, thereby enabling classification and, optionally, other analyses of the at least part of defects. In some cases both phases can be implemented by the same inspection tool, and, in some other cases, these two phases are implemented by different inspection tools.

The term "Metrology" used in this specification should be expansively construed to cover any kind of measuring characteristics and features in a specimen provided by using examination and/or metrology tools during or after manufacture of the specimen to be inspected. By way of non-limiting example, the metrology process can include generating a measurement recipe and/or performing runtime measurement, for example by scanning (in a single or in multiple scans), reviewing, measuring and/or other operations provided with regard to the specimen or parts thereof using the same or different tools. Measurement results such as measured images are analyzed for example, by employing image-processing techniques. Note that, unless specifically stated otherwise, the term "metrology" or derivatives thereof used in this specification are not limited with respect to measurement technology, measurement resolution or size of inspection area.

There is a need in the art to improve the process of metrology, for example by improving the utilization of design data; by improving the preparation of examination recipes; or by improving the definition of metrology objects and metrology operations used for metrology.

GENERAL DESCRIPTION

In accordance with certain aspects of the presently disclosed subject matter, there is provided an examination system capable of performing metrology operations related to a specimen, comprising: a computer-based recipe unit configured to generate an examination recipe in accordance with a metrology application, the examination recipe specifying one or more metrology objects and one or more metrology operations related to the metrology application, wherein at least one of the group consisting of the one or more metrology objects and the one or more metrology operations is specified with reference to design data; and a metrology tool comprising a processing circuitry, wherein the metrology tool is configured to: obtain an image-based representation of the specimen comprising image-based representation of at least first metrology object selected from the one or more metrology objects, and a design-based representation of the specimen comprising design-based representation of the at least first metrology object; map between the design-based representation of the at least first metrology object and the image-based representation of the at least first metrology object; and perform at least first metrology operation of the one or more metrology operations according to the examination recipe, wherein the at least first metrology operation is specified in the examination recipe as related to the at least first metrology object and to be performed on at least the image-based representation of the specimen, and wherein the at least first metrology operation is performed using the mapping.

In addition to the above features, the examination system according to this aspect of the presently disclosed subject matter can comprise one or more of features (a) to (n) listed below, in any desired combination or permutation which is technically possible:

a. The system can further comprise an examination tool configured to use the examination recipe to capture the image-based representation of the specimen.
b. The recipe unit can be implemented as part of the metrology tool.
c. The metrology application can be selected from a group comprising: Measurement-Based Inspection (MBI), Critical Dimension Uniformity (CDU), 3-Dimentional Uniformity (3DU), CAD Awareness (CADA) and Overlay (OVL).
d. The system can further comprise a Graphical user interface (GUI) configured to enable a user to select the metrology application from one or more metrology applications and the at least first metrology object related to the metrology application.
e. The examination tool can be further configured to capture one or more test image-based representations of the specimen using the examination recipe, and the mapping and the performing can be performed with respect to the test image-based representations to verify the examination recipe.
f. The examination recipe can comprise one or more illumination conditions to be used by the examination tool for capturing the image-based representation of the specimen, the one or more illumination conditions derived with respect to the metrology application and the specimen.
g. Each of the one or more metrology objects can be selected from a group comprising: a structural element, a virtual object, and a ghost object. The virtual object is a metrology object that does not have an original design-based representation thereof, and the ghost object is a metrology object that only has design-based representation thereof.
h. The one or more metrology objects can comprise one or more initial objects and one or more derived objects resulted from performing at least one metrology operation defined as related to the initial objects, and the one or more metrology operations can comprise at least one operation defined related to the one or more derived objects.
i. The metrology tool can be configured to map between the design-based representation and the image-based representation of the at least first metrology object by registering the image-based representation of the specimen with the design-based representation of the specimen to obtain position calibration data, identifying at least a pair of corresponding design-based representation and image-based representation of the at least first metrology object using the position calibration data and assigning a unique identifier to each of the at least a pair.
j. The one or more metrology objects can be specified on the design-based representation of the specimen and the one or more metrology operations can be specified to be performed on the image-based representation of the specimen, or on both the image-based representation of the specimen and the design-based representation of the specimen.
k. The one or more metrology objects can be specified on the image-based representation of the specimen and the one or more metrology operations can be specified to be performed on both the image-based representation of the specimen and the design-based representation of the specimen.
l. The design data can be pre-acquired design data, the one or more metrology objects are defined on the pre-acquired design data, and at least one of the metrology operations is defined related to the one or more metrology objects. The metrology tool is further configured to: search on the design-based representation of the specimen to identify the at least first metrology object.
m. The one or more metrology objects can comprise at least second metrology object having only a design-based representation thereof on the design-based representation of the specimen, and at least second metrology operation of the one or more metrology operations is specified to be related to the at least second metrology object and to be performed on the image-based representation or on both the design-based representation and the image-based representation of the specimen. The metrology tool can be further configured to: register the design-based representation of the specimen and the image-based representation of the specimen to obtain position calibration data; identifying a position indication of the at least second metrology object on the image-based representation of the specimen using the position calibration data; and perform the at least second metrology operation according to definition of the at least second metrology operation in the examination recipe using the position indication.
n. The one or more metrology objects can comprise at least one defect object having only an image-based representation thereof on the image-based representation of the specimen, and at least third metrology operation of the one or more metrology operations is specified to be related to the at least one defect object and to be performed on both the image-based representation and the design-based representation of the specimen. The metrology tool can be further configured to: register the design-based representation of the specimen and the image-based representation of the specimen to obtain position calibration data; identify a position indication of the at least one defect object on the design-based representation of the specimen using the position calibration data; and perform the at least third metrology operation on both the image-based representation and the design-based representation of the specimen according to definition of the at least second metrology operation in the examination recipe using the position indication.

In accordance with another aspect of the presently disclosed subject matter, there is provided a computerized method of performing metrology operations related to a specimen, comprising: generating, by a computer-based recipe unit, an examination recipe in accordance with a metrology application, the examination recipe specifying one or more metrology objects and one or more metrology operations related to the metrology application, wherein at least one of the group consisting of the one or more metrology objects and the one or more metrology operations is specified with reference to design data; obtaining, by a metrology tool, an image-based representation of the specimen comprising image-based representation of at least first metrology object selected from the one or more metrology objects, and a design-based representation of the specimen comprising design-based representation of the at least first metrology object; mapping, by the metrology tool, between the design-based representation of the at least first metrology object and the image-based representation of the at least first metrology object; and performing, by the metrology tool, at least first metrology operation of the one or more metrology operations according to the examination recipe, wherein the at least first metrology operation is specified as related to the at least first metrology object and to be performed on at least the image-based representation of the specimen, and wherein the at least first metrology operation is performed using the mapping.

This aspect of the disclosed subject matter can comprise one or more of features (a) to (n) listed above with respect to the examination system, mutatis mutandis, in any desired combination or permutation which is technically possible.

In accordance with another aspect of the presently disclosed subject matter, there is provided a recipe unit, comprising: a Graphical user interface (GUI) configured to define a metrology application, and define one or more metrology objects and one or more metrology operations related to the metrology application, wherein at least one of the group consisting of the one or more metrology objects and the one or more metrology operations is defined with reference to design data, and wherein the one or more metrology objects comprise at least one of a virtual object and a ghost object, wherein the virtual object is a metrology object that does not have an original design-based representation thereof, and the ghost object is a metrology object that only has design-based representation thereof; and a processing circuitry operatively connected to the GUI, the processing circuitry comprising a memory and a processor operatively coupled thereto and configured to generate an examination recipe in accordance with definitions of the metrology application, the one or more metrology objects and one or more metrology operations.

In addition to the above features, the recipe unit according to this aspect of the presently disclosed subject matter can comprise one or more of features (i) to (ii) listed below, in any desired combination or permutation which is technically possible:

(i). The one or more metrology objects can comprise a ghost object, and at least one metrology operation of the one or more metrology operations is defined to be related to the ghost object and to be performed on the image-based representation or on both the design-based representation of the specimen and the image-based representation.

(ii). The one or more metrology objects can comprise a virtual object which is a defect object having only an image-based representation thereof on the image-based representation of the specimen, and at least one metrology operation of the one or more metrology operations is defined to be related to the defect object and to be performed on both the image-based representation and the design-based representation of the specimen.

This aspect of the disclosed subject matter can further comprise one or more of features (a) to (n) listed above with respect to the examination system, mutatis mutandis, in any desired combination or permutation which is technically possible.

In accordance with certain aspects of the presently disclosed subject matter, there is provided a method of performing metrology operations on at least one representation of a specimen using a processor operatively connected to a memory, the method comprising: accommodating, in the memory, definitions of one or more metrology objects and one or more metrology operations, wherein at least one of the group consisting of the one or more metrology objects and the one or more metrology operations is defined with reference to design data; accommodating, in the memory, a representation group comprising a design-based representation of the specimen and an image-based representation of the specimen; wherein the design-based representation of the specimen comprises design-based representation of at least first metrology object of the one or more metrology objects and the image-based representation of the specimen comprises image-based representation of the at least first metrology object of the one or more metrology objects, and wherein the one or more metrology operations include at least first metrology operation, the at least first metrology operation being defined to be related to the at least first metrology object and to be performed on at least the image-based representation of the specimen; mapping, by the processor, between the design-based representation of the at least first metrology object and the image-based representation of the at least first metrology object; and performing, by the processor, the at least first metrology operation according to definition of the at least first metrology operation using the mapping.

In addition to the above features, the method according to this aspect of the presently disclosed subject matter can comprise one or more of features (i) to (xiv) listed below, in any desired combination or permutation which is technically possible:

(i). The design data can be the design-based representation of the specimen, and the one or more metrology operations can be defined related to at least one of the metrology objects.

(ii). The design data can be pre-acquired design data, the one or more metrology objects can be defined on the pre-acquired design data, and at least one of the metrology operations can be defined related to the one or more metrology objects. The method can further comprise: searching on the design-based representation of the specimen to identify the at least first metrology object.

(iii). The one or more metrology objects can include one or more initial objects each initially defined on the design data or image data.

(iv). The one or more metrology objects can further include one or more derived objects resulted from performing at least one of the metrology operations defined related to the initial objects, and the one or more metrology operations can include at least one operation defined related to the derived objects.

(v). The one or more metrology objects can include one or more of the following: structural elements, virtual objects, and ghost objects, wherein the virtual objects are metrology objects that do not have an original design-based representation thereof, and ghost objects are metrology objects that only have design-based representation thereof.

(vi). The one or more metrology operations can be selected from a group comprising: search operation, measurement operation, and Region Of Interest (ROI) operation.

(vii). The measurement operation can be selected from a group comprising: Area, Critical Dimension (CD), Distance, Center of Gravity (CoG), Gray Level (GL), Contact Hole Analysis (CHA), 'Distance from image to design', and Arithmetic calculations.

(viii). The one or more metrology objects can be defined on the design-based representation of the specimen and the metrology operations can be defined to be performed on the image-based representations of the specimen, or on both the image-based representations of the specimen and the design-based representation of the specimen.

(ix). The one or more metrology objects can be defined on the image-based representations of the specimen and the metrology operations can be defined to be performed on both the image-based representations of the specimen and the design-based representation of the specimen.

(x). The mapping can be performed by registering the image-based representations of the specimen with the design-based representation of the specimen to obtain position calibration data, identifying pairs of corresponding design-based representation and image-based representation of the at least first metrology object using the position calibration data and assigning a unique identifier to each of the pairs.

(xi). The definitions of one or more metrology operations can include a representation to perform the one or more metrology operations which is determined by one or more of the following factors: the type of the metrology operations, a representation where the metrology objects related to the metrology operations are defined and one or more additional parameters defined by a user.

(xii). At least one of the metrology objects is associated with an attribute of context indicative of a parent object thereof.

(xiii). At least second metrology object of the one or more metrology objects can have only a design-based representation thereof on the design-based representation of the specimen, and at least second metrology operation of the one or more metrology operations can be defined related to the at least second metrology object and to be performed on the image-based representation or on both the design-based representation of the specimen and the image-based representation. The method can comprise:
 registering, by the processor, the design-based representation of the specimen and the image-based representation of the specimen to obtain position calibration data;
 identifying, by the processor, a position indication of the at least second metrology object on the image-based representation of the specimen using the position calibration data; and
 performing, by the processor, at least second metrology operation of the one or more metrology operations related to the at least second metrology object according to definition of the at least second metrology operation using the position indication.

(xiv). The one or more metrology objects can include at least one defect object having only an image-based representation thereof on the image-based representation of the specimen, and at least third metrology operation of the one or more metrology operations can be defined related to the at least one defect object and to be performed on both the image-based representation and the design-based representation of the specimen. The method can comprise:
 registering, by the processor, the design-based representation of the specimen and the image-based representation of the specimen to obtain position calibration data;
 identifying, by the processor, a position indication of the at least one defect object on the design-based representation of the specimen using the position calibration data; and
 performing, by the processor, the at least third metrology operation on both the image-based representation and the design-based representation of the specimen using the position indication.

In accordance with another aspect of the presently disclosed subject matter, there is provided a computerized system capable of generating performing metrology operations on at least one representation of a specimen, the system comprising a processing circuitry that comprises a processor and a memory operatively coupled thereto, wherein: i) the memory is configured to: store definitions of one or more metrology objects and one or more metrology operations, wherein at least one of the group consisting of the one or more metrology objects and the one or more metrology operations is defined with reference to design data; and store a representation group comprising a design-based representation of the specimen and an image-based representation of the specimen; wherein the design-based representation of the specimen comprises design-based representation of at least first metrology object of the one or more metrology objects and the image-based representation of the specimen comprises image-based representation of the at least first metrology object of the one or more metrology objects, and wherein the one or more metrology operations include at least first metrology operation, the at least first metrology operation being defined to be related to the at least first metrology object and to be performed on at least the image-based representation of the specimen; and ii) the processing circuitry is configured to: map between the design-based representation of the at least first metrology object and the image-based representation of the at least first metrology object; and perform the at least first metrology operation according to definition of the at least first metrology operation using the mapping.

This aspect of the disclosed subject matter can comprise one or more of features (i) to (xiv) listed above with respect to the method, mutatis mutandis, in any desired combination or permutation which is technically possible.

In accordance with another aspect of the presently disclosed subject matter, there is provided a non-transitory computer readable storage medium tangibly embodying a program of instructions that, when executed by a computer, cause the computer to perform a method of generating performing metrology operations on at least one representation of a specimen, the method comprising: accommodating, in the memory, definitions of one or more metrology objects and one or more metrology operations, wherein at least one of the group consisting of the one or more metrology objects and the one or more metrology operations is defined with reference to design data; accommodating, in the memory, a representation group comprising a design-based representation of the specimen and an image-based representation of the specimen; wherein the design-based representation of the specimen comprises design-based representation of at least first metrology object of the one or more metrology objects and the image-based representation of the specimen comprises image-based representation of the at least first metrology object of the one or more metrology objects, and wherein the one or more metrology operations include at least first metrology operation, the at least first metrology operation being defined to be related to the at least first metrology object and to be performed on at least the image-based representation of the specimen; mapping, by the processor, between the design-based representation of the at least first metrology object and the image-based representation of the at least first metrology object; and performing, by the processor, the at least first metrology operation according to definition of the at least first metrology operation using the mapping.

This aspect of the disclosed subject matter can comprise one or more of features (i) to (xiv) listed above with respect to the method, mutatis mutandis, in any desired combination or permutation which is technically possible.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

In the following detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "accommodating", "defining", "mapping", "performing", "registering", "identifying", "assigning", "associating", "generating", "using", "obtaining", "specifying", "enabling", "selecting", "capturing", "searching", or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities including, by way of non-limiting example, the examination system, metrology tool, examination tool, recipe unit and parts thereof as well as the processing circuitry therein disclosed in the present application.

The terms "non-transitory memory" and "non-transitory storage medium" used herein should be expansively construed to cover any volatile or non-volatile computer memory suitable to the presently disclosed subject matter.

The term "defect" used in this specification should be expansively construed to cover any kind of abnormality or undesirable feature formed on or within a specimen.

The term "design data" used in the specification should be expansively construed to cover any data indicative of hierarchical physical design (layout) of a specimen. Design data can be provided by a respective designer and/or can be derived from the physical design (e.g. through complex simulation, simple geometric and Boolean operations, etc.). Design data can be provided in different formats as, by way of non-limiting examples, GDSII format, OASIS format, etc. Design data can be presented in vector format, grayscale intensity image format or otherwise.

It is appreciated that, unless specifically stated otherwise, certain features of the presently disclosed subject matter, which are described in the context of separate embodiments, can also be provided in combination in a single embodiment. Conversely, various features of the presently disclosed subject matter, which are described in the context of a single embodiment, can also be provided separately or in any suitable sub-combination. In the following detailed description, numerous specific details are set forth in order to provide a thorough understanding of the methods and apparatus.

Figure 1:
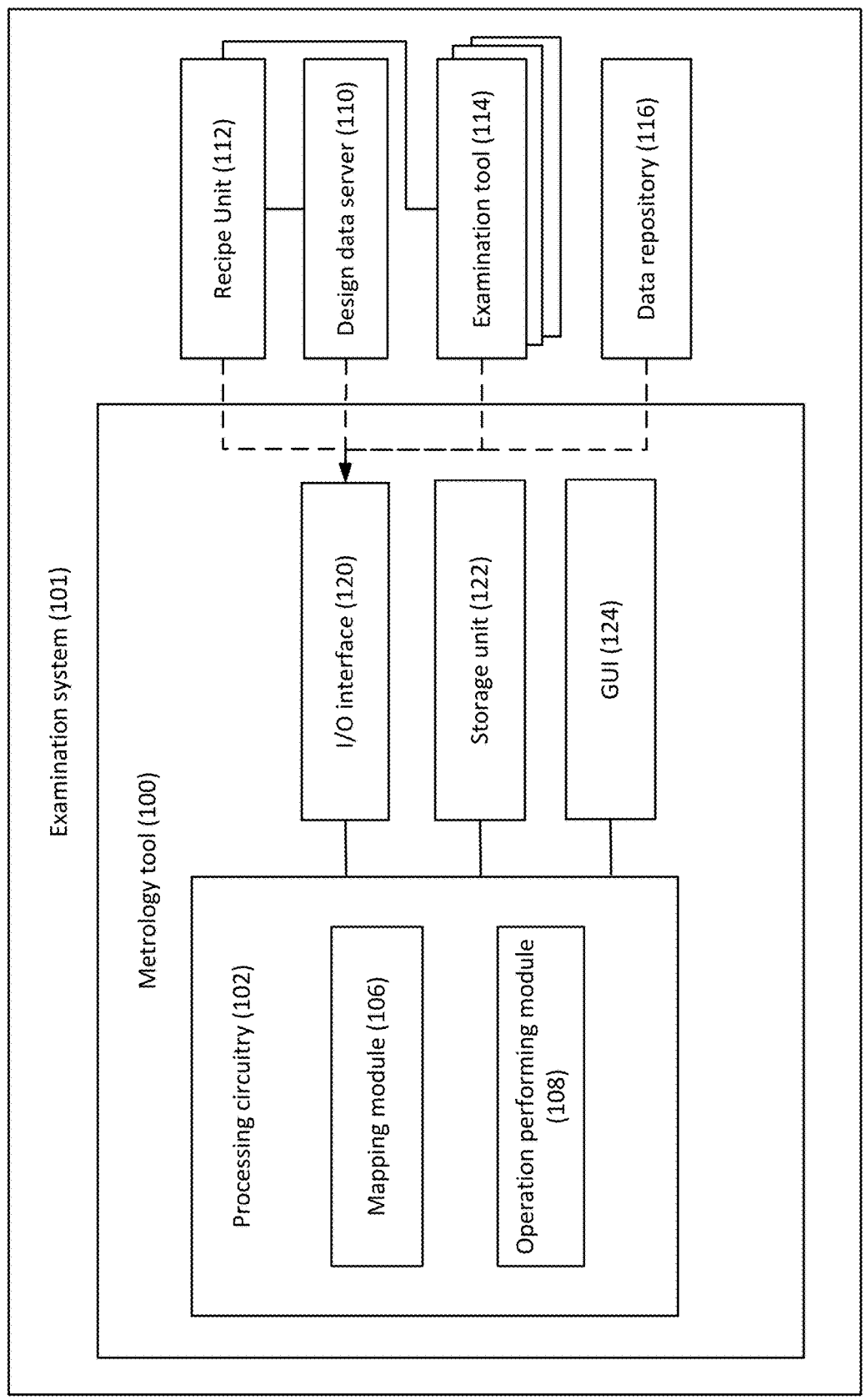
FIG. 1 illustrates a block diagram of an examination system in accordance with certain embodiments of the presently disclosed subject matter.

Bearing this in mind, attention is drawn to FIG. 1 illustrating a block diagram of an examination system in accordance with certain embodiments of the presently disclosed subject matter. The examination system 101 illustrated in FIG. 1 can be used for examination and performing metrology related operations with respect to a specimen (e.g. of a wafer and/or parts thereof) as a part of specimen fabrication. The examination can be a part of the object fabrication and can be carried out during manufacturing the object or afterwards. According to certain embodiments, the illustrated examination system 101 comprises a computer-based metrology tool 100 capable of (and can be configured for) performing metrology operations related to a specimen. In some embodiments, the metrology tool 100 can be used for performing metrology operations on at least one representation of a specimen using design data.

Metrology tool 100 can be operatively connected to one or more examination tools 114 that can be configured to use an examination recipe to capture image-based representation of the specimen. The term "examination tools" used herein should be expansively construed to cover any tools that can be used in examination-related processes including, by way of non-limiting example, imaging, scanning (in a single or in multiple scans), sampling, reviewing, measuring, classifying and/or other processes provided with regard to the specimen or parts thereof. The one or more examination tools 114 can include one or more inspection tools and/or one or more review tools. In some cases, at least one of the examination tools 114 can be an inspection tool configured to scan an entire specimen (e.g., an entire wafer or at least an entire die) to capture inspection images (typically, at relatively high-speed and/or low-resolution) for detection of potential defects. In some cases, at least one of the examination tools 114 can be a review tool, which is configured to capture review images of at least part of defects detected by inspection tools for ascertaining whether a potential defect is indeed a defect. Such a review tool is usually configured to inspect fragments of a die, one at a time (typically, at relatively low-speed and/or high-resolution). Inspection tool and review tool can be different tools located at the same or at different locations, or a single tool operated in two different modes. In some cases at least one examination tool can have metrology capabilities.

Without limiting the scope of the disclosure in any way, it should also be noted that the examination tools 114 can be implemented as inspection machines of various types, such as optical imaging machines, electron beam inspection machines and so on.

Metrology tool 100 can be further operatively connected to Design data server 110 (e.g., CAD server) which is configured to store and provide design data characterizing the specimen. In some cases, Metrology tool 100 can be operatively connected to one or more Data repositories 116 which is configured to store data (and/or derivatives thereof) produced by the examination tools 114 and/or the Design data server 110.

Metrology tool 100 comprises a processing circuitry 102 operatively connected to a hardware-based I/O interface 120. Processing circuitry 102 is configured to provide all processing necessary for operating metrology tool 100 which is further detailed with reference to FIGS. 2-3 and 7. Processing circuitry 102 comprises a processor (not shown separately) and a memory (not shown separately). The processor of processing circuitry 102 can be configured to execute several functional modules in accordance with computer-readable instructions implemented on a non-transitory computer-readable memory comprised in the processing circuitry. Such functional modules are referred to hereinafter as comprised in the processing circuitry 102.

Functional modules comprised in the processor can include a Mapping module 106, and an Operation performing module 108, which are operatively connected with each other. An examination recipe specifying/defining one or more metrology objects and one or more metrology operations related to a metrology application can be accommodated in a memory (e.g., either in the memory as comprised in the Processing circuitry 102 or in the Storage unit 122). At least one of the group consisting of the one or more metrology objects and the one or more metrology operations can be defined with reference to design data. According to certain embodiments, the examination recipe, including definitions of the metrology objects and metrology operations can be received from an external system or storage device, or alternatively it can be generated by a recipe unit 112 during a recipe setup phase, as will be described below.

According to certain embodiments, metrology tool 100 can be operatively connected to a computer-based recipe unit 112. The recipe unit 112 can be configured to generate an examination recipe in accordance with a metrology application. The examination recipe can specify/define one or more metrology objects and one or more metrology operations related to the metrology application. The one or more metrology objects and/or the one or more metrology operations can be specified/defined with reference to design data. In some embodiments, the recipe unit can be implemented as part of the metrology tool 100.

A metrology application used herein refers to what a customer/user is interested to measure in general with respect to the specimen. By way of non-limiting example, a metrology application can be selected from a group of metrology applications comprising: Measurement-Based Inspection (MBI), Critical Dimension Uniformity (CDU), 3-Dimentional Uniformity (3DU), CAD Awareness (CADA) and Overlay (OVL). MBI refers to defect inspection using measurement. One example of MBI can be detection of etch residue in a bottom of a trench. CDU refers to uniformity measurement related to critical dimension. One example of CDU can be to create a uniformity map of the offset between two contacts. Overlay refers to measurement of the overlay shift between multiple layer patterns. One example of overlay can be to find the nominal overlay error between two layers on the edge of the wafer. 3DU refers to measurement of 3D structures, such as, e.g., height measurements. CADA refers to the integration of CAD into SEM-based defect inspection.

According to certain embodiments, the recipe unit 112 can comprise a Graphical user interface (GUI) (not shown separately in FIG. 1) and a processing circuitry (not shown separately in FIG. 1) operatively connected to the GUI. The GUI can be configured to (e.g., enable a user to) define a metrology application, and define one or more metrology objects and one or more metrology operations related to the metrology application. The one or more metrology objects and/or the one or more metrology operations can be specified/defined with reference to design data. In some embodiments, the one or more metrology objects can comprise at least one of a virtual object and a ghost object. The virtual object refers to a metrology object that does not have an original design-based representation thereof, as will be described in further detail below with reference to FIGS. 2 and 4. The ghost object refers to a metrology object that only has design-based representation thereof, as will be described in further detail below with reference to FIG. 3. The processing circuitry comprises a memory and a processor operatively coupled thereto and is configured to generate an examination recipe in accordance with definitions of the metrology application, the one or more metrology objects and one or more metrology operations.

In some embodiments, the examination recipe, including the definitions of the metrology object(s) and metrology operation(s) can be generated by the recipe unit 112 during a recipe setup phase, and can be used by the metrology tool 100 for performing metrology operations during a runtime measurement phase. It is to be noted that the term examination recipe should be expansively construed to cover any recipe that can be used for examining a specimen, including recipe(s) for inspection, review, as well as metrology related operations, etc. In some cases, the examination recipe can comprise one or more illumination conditions to be used by the examination tool for capturing the image-based representation of the specimen. The one or more illumination conditions can be derived with respect to the given metrology application and the specimen. By way of example, the illumination condition for Overlay application can be See Through or HAR. By way of another example, the illumination condition for CDU application can be Low current. By way of another example, the illumination condition for MBI application can be High current.

The metrology objects and metrology operations can be defined with respect to representation(s) of the specimen. In some embodiments, a user is presented with a representation of the specimen in a visual manner (for example, by a display forming part of a GUI as comprised in the recipe unit 112). The customer/user may define, via the GUI, one or more metrology objects by selecting and/or marking metrology objects residing in the specimen representation—for example, by operating a computer stylus or mouse. The user may further define, via the GUI, metrology operations to be carried out with respect to the metrology objects, for example, by selecting an option from a drop-down list or menu or any other visual representations of option listing.

A representation group comprising a design-based representation of the specimen and an image-based representation of the specimen can also be accommodated in the memory (e.g., either in the memory as comprised in the processing circuitry 102 or in the Storage unit 122). According to certain embodiments, the design-based representation (also referred to as design representation) of the specimen can comprise design-based representation of at least a first metrology object of the one or more metrology objects, and the image-based representation (also referred to as image representation) of the specimen can comprise image-based representation of the at least first metrology object of the one or more metrology objects. In other words, there exists at least one metrology object, i.e., the at least first metrology object, which has two corresponding representations on both design and image representation of the specimen.

The metrology tool 100 can be configured to obtain an image-based representation of the specimen comprising image-based representation of at least first metrology object selected from the one or more metrology objects, and a design-based representation of the specimen comprising design-based representation of the at least first metrology object.

The image-based representation of the specimen can be obtained via the examination tool 114. The examination tool 114 can be configured to use the examination recipe (e.g., generated by the recipe unit 112) to capture the image-based representation of the specimen, e.g., during runtime measurement phase. The image-based representation of the specimen can comprise image-based representation of at least first metrology object selected from the one or more metrology objects. The image-based representation of the specimen can be image data resulted from imaging of the specimen, including one or more images of the specimen. The images can be resulted from different examination modality(s), and the present disclosure is not limited by the inspection and metrology technology used for generating the images. In certain embodiments, the images include inspection images.

The design-based representation of the specimen can be obtained from the Design data server 110, and can include design data characterizing the specimen. The design-based representation can be selected from the following: the physical design layout (e.g., CAD clip) of the specimen, a raster image and a simulated image derived from the design layout. It is to be noted that, unless specified otherwise, the terms "design data", "design-based representation" and "design representation" are used interchangeably within the present disclosure. The terms "image data", "image-based representation" and "image representation" are also used interchangeably within the present disclosure. In certain embodiments of the below description, image-based representation of a metrology object is also referred to as image metrology object or image object. Design-based representation of a metrology object is also referred to as design metrology object or design object.

The one or more metrology operations can include at least a first metrology operation. The at least first metrology operation can be defined to be related to the at least first metrology object and to be performed on at least the image-based representation of the specimen (e.g., related to the image-based representation of the at least first metrology object).

Upon obtaining the design-based representation and image-based representation of the specimen, e.g., during runtime measurement phase, the Mapping module 106 can be configured to map between the design-based representation of the at least first metrology object and the image-based representation of the at least first metrology object. Operation performing module 108 can be configured to perform the at least first metrology operation according to the examination recipe (e.g., according to definition of the at least first metrology operation in the recipe) using the mapping. The at least first metrology operation is specified in the examination recipe as related to the at least first metrology object and to be performed on at least the image-based representation of the specimen, and the at least first metrology operation is performed using the mapping between the two representations of the at least first metrology object. Operations of the metrology tool 100, processing circuitry 102 and the functional blocks therein will be further detailed with reference to FIGS. 2-3 and 7. It is to be noted that in some cases, the functionality of the operation performing module 108 can be at least partly integrated with the examination tools 114.

According to certain embodiments, the generated examination recipe can be verified prior to be used in runtime measurement. In such cases, the examination tool can be configured to capture one or more test image-based representations of the specimen using the examination recipe, and the mapping and the performing as described above can be performed with respect to the test image-based representations to verify the examination recipe.

The terms "metrology object" or "object" used in this specification should be expansively construed to cover any metrology target as an element of a pattern in a layer on a semiconductor wafer under fabrication, that is defined on design data and/or image data. Metrology object(s) can be further defined according to different perspectives, such as, e.g., whether the metrology object has one representation or two corresponding representations, whether it is defined on design data or image data, whether it is an initial object or a derived object, and whether it is a structural element, a virtual object, a ghost object or any other kind of objects, etc., as will be described below in details with respect to FIG. 2.

The terms "metrology operation" or "operation" used in this specification should be expansively construed to cover any metrology operation procedure used to extract metrology information relating the metrology objects. By way of example, metrology information to be extracted can be indicative of region or object of interest, dimensions (line widths, line spacing, size of the element, edge roughness, gray level statistics, etc.) and/or shape of metrology objects and/or distances within or between metrology objects, related angles, and/or overlay information associated with metrology objects corresponding to different design levels, etc. The metrology operations can include measurement operations which in turn can include structure-based measurements, rule-based measurements, measurements based on templates, measurements associated with geometric properties such as distances and angles, and/or other measurements, as will be described in details below.

In some embodiments, the metrology tool 100 can comprise a GUI 124 which is configured to enable a user to select, during runtime phase, a metrology application from one or more metrology applications and select the at least first metrology object related to the metrology application, optionally, also the at least first metrology operation. The GUI 124 can be implemented in a similar manner as described above with reference to the GUI of the recipe unit 112, and can be configured to enable user-specified inputs related to metrology tool 100. The customer/user may perform the selection by, e.g., marking metrology objects residing in the specimen representation with, e.g., a computer stylus or mouse. The customer/user may select metrology operations to be carried out with respect to the metrology objects, for example, by choosing an option from a drop-down list or menu or any other visual representations of option listing. In some cases, GUI 124 may be implemented as a graphical interface separately from the GUI of the recipe unit 112. In some other cases, there can be one GUI used for both setting up the examination recipe as well as runtime measurement. For instance, GUI 124 can function as GUI of the recipe unit 112 or vice versa.

Alternatively or additionally, the metrology objects and/or operations as defined during recipe setup phase and/or as selected during runtime measurement phase can be resulted from an appropriate analysis of design data and/or image data. Optionally, a user can specify the metrology objects, while corresponding metrology operations can be, in response, automatically specified or selected, in accordance with predefined rules, among predefined operations associated to different metrology objects. In some cases, metrology objects can be specified in design coordinates. In other cases, metrology objects can be specified as structural elements characterized by shape, size and, optionally, location, geometrical relations between elements, relative position within the design representation or image representation. Further embodiments and examples with respect to metrology objects and metrology operations are described below with respect to FIG. 2.

Metrology tool 100 can be configured to receive, via I/O interface 102, data (and/or derivatives thereof) stored or produced by the examination tools 114 and/or data stored in design data server 110 and/or data stored in one or more data repositories 116 and/or data stored in recipe unit 112.

As aforementioned, by way of example, a specimen can be scanned by an examination tool 114 to capture image-based representation of the specimen. The resulting image data and/or derivatives thereof) can be transmitted—directly or via one or more intermediate systems—to Metrology sub system 100. The present disclosure is not limited by the examination technology.

Metrology tool 100 can be further configured to process the received image data provided by the examination tools 114 and/or the design data provided by the design data server 110, and send, via I/O interface 102, the results (or part thereof) to a storage system which may be the same as the data repositories 116, or may be in addition or in lieu of the data repositories 116. The results can also be sent to any of the examination tool(s) and/or an external system, and/or a computer-based graphical user interface (GUI) 124 for rendering the results.

Those versed in the art will readily appreciate that the teachings of the presently disclosed subject matter are not bound by the system illustrated in FIG. 1; equivalent and/or modified functionality can be consolidated or divided in another manner and can be implemented in any appropriate combination of software with firmware and hardware.

It is noted that the metrology system illustrated in FIG. 1 can be implemented in a distributed computing environment, in which the aforementioned functional modules shown in FIG. 1 can be distributed over several local and/or remote devices, and can be linked through a communication network. It is further noted that although the recipe unit 112, the examination tools 114, data repositories 116, design data server 110 are illustrated as being external to the Metrology tool 100 and operate in data communication with system 100 via I/O interface 120, in some other embodiments, at least part of the aforementioned units can be implemented as part of the Metrology tool 100.

For instance, Metrology tool 100 can be implemented as stand-alone computer(s) to be used in conjunction with the examination tools 114. Alternatively, the respective functions of metrology tool 100 can, at least partly, be integrated with one or more examination tools 114 thereby facilitating and enhancing the functionalities of the examination tools 114 in metrology-related processes. In such cases, components of the metrology tool 100 may form part of examination tool 114. By way of one example, the operation performing module 108 can be implemented or integrated as part of the examination tools 114. By way of another example, processing circuitry 102 and storage unit 122 may form part of the processing circuitry and storage, respectively, of examination tool 114; and the I/O interface and GUI of the examination tool 114 may function as I/O interface 120 and GUI 124. Similarly, the recipe unit 112 can be implemented as stand-alone computer(s) to be used in conjunction with the Metrology tool 100, or alternatively, the respective functions of recipe unit 112 can, at least partly, be integrated with the Metrology tool 100. For instance, the recipe unit 112 can be implemented as part of the metrology tool 100.

Figure 2:
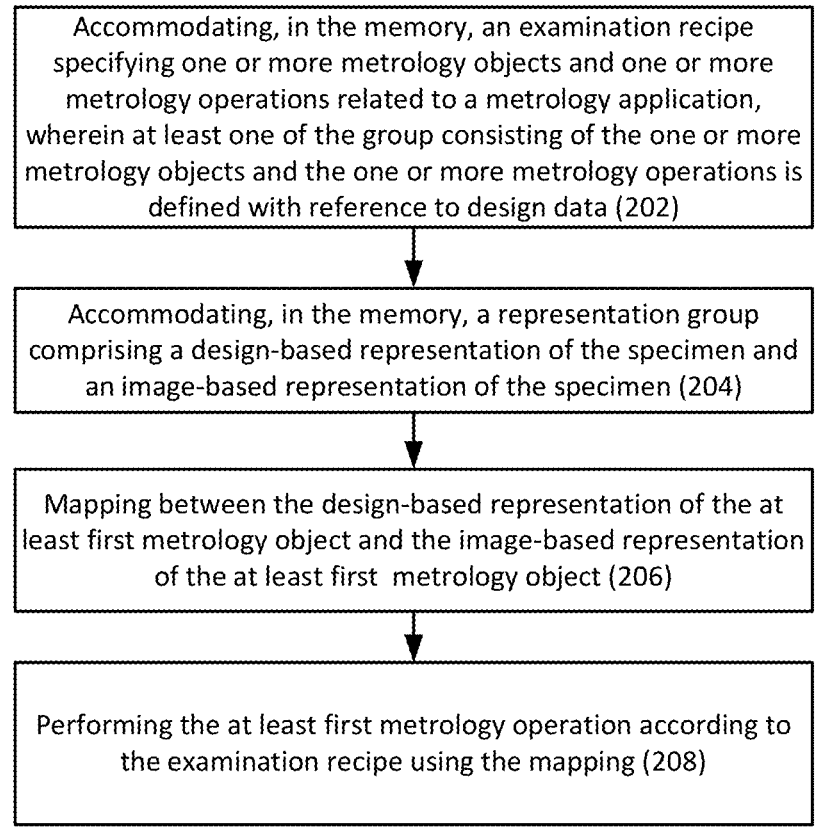
FIG. 2 illustrates a generalized flow chart of performing metrology operations on at least one representation of a specimen in accordance with certain embodiments of the presently disclosed subject matter.

Referring to FIG. 2, there is illustrated a generalized flowchart of performing metrology operations on at least one representation of a specimen in accordance with certain embodiments of the presently disclosed subject matter.

An examination recipe specifying one or more metrology objects and one or more metrology operations related to a metrology application can be accommodated (202) in the memory (e.g., either in the memory as comprised in the processing circuitry 102 or in the Storage unit 122 as illustrated in FIG. 1). At least one of the group consisting of the one or more metrology objects and the one or more metrology operations can be defined/specified using or with reference to design data. As aforementioned, the one or more metrology objects and one or more metrology operations can be defined via the recipe unit 112 during recipe setup phase. The examination recipe can be generated by the recipe unit 112 in accordance with the metrology application, the examination recipe specifying the one or more metrology objects and one or more metrology operations related to the metrology application.

For purpose of illustration only, certain embodiments of the following description are provided with respect to CAD clips. Embodiments are, likewise, applicable to other formats and representations of design data. In some embodiments (e.g. if design data are presented in vector format), intermediate processing of design data can be required.

As aforementioned, a metrology object can refer to any metrology target or element that is defined on design data and/or image data, e.g., via recipe unit 112. Metrology object can be an object of interest or a pattern of interest to be measured. According to certain embodiments, the one or more metrology objects as defined can include one or more initial objects that are initially defined or identified on design data and/or image data. The one or more operations can include at least one operation defined related to the initial objects. By way of example, the initial objects can include an object of Field of View (FOV) indicative of the extent of observable range or scope on the design data and/or the image data within which subsequent objects and operations can be defined or performed. By way of another example, the initial objects can include one or more objects that originally exist on the design data and/or image data, such as, e.g., design structural elements on a CAD clip, and/or segmented structural elements obtained through a segmentation process on an inspection image. Such original objects can be specified by a user or automatically selected by the system as the initial objects.

A structural element used herein refers to any original object or element on the design data or image data that has a geometrical shape or geometrical structure with a contour, or a geometrical shape combined with insertion of other structural elements. A structural element that is located on the design data can be referred to as a design structural element. A design structural element can be presented, e.g., in the form of a polygon. A structural element that is located in the image data can be referred to as an image structural element. A structural element can be defined by the user, or can be defined automatically, for example using rule-based or machine-learning techniques.

According to certain embodiments, the one or more metrology objects can further include one or more derived objects that are resulted from performing at least one of the metrology operations defined related to the initial objects. The one or more metrology operations can include at least one operation defined related to the derived objects. By way of example, an initial object can be defined as FOV on the design data. An operation that is defined related to the initial object of FOV can be, e.g., a search operation which upon being performed can search for a specified design structural element or pattern of interest (e.g., a hotspot or other repetitive pattern to be measured) within the FOV. The search operation, once performed, may result in one or more structural elements or patterns of interest (if any) which meet the search query. These resulted objects are referred to as the derived objects, i.e., objects derived from performing metrology operations, as compared to the initial objects that are initially defined. Further metrology operations can in turn be defined related to the derived objects. For instance, an operation of Center of Gravity (CoG) can be defined related to the derived objects resulted from the search operation, e.g., the structural elements as being found. The CoG operation will result in an object which is derived therefrom, i.e., a center point of each structural element as being found. Note that objects such as, e.g., the center points, do not originally exist in the design data of the specimen and therefore are sometimes referred to as being "virtual".

It is to be noted that the term "virtual object" used herein should be expansively construed to cover any metrology object that does not have an original design-based representation thereof. Virtual objects can be defined on both design data or image data. According to certain embodiments, virtual objects can include derived objects that are resulted from performing operations and are not originally present in design data (e.g., the CoG objects as exemplified above).

Figure 4:
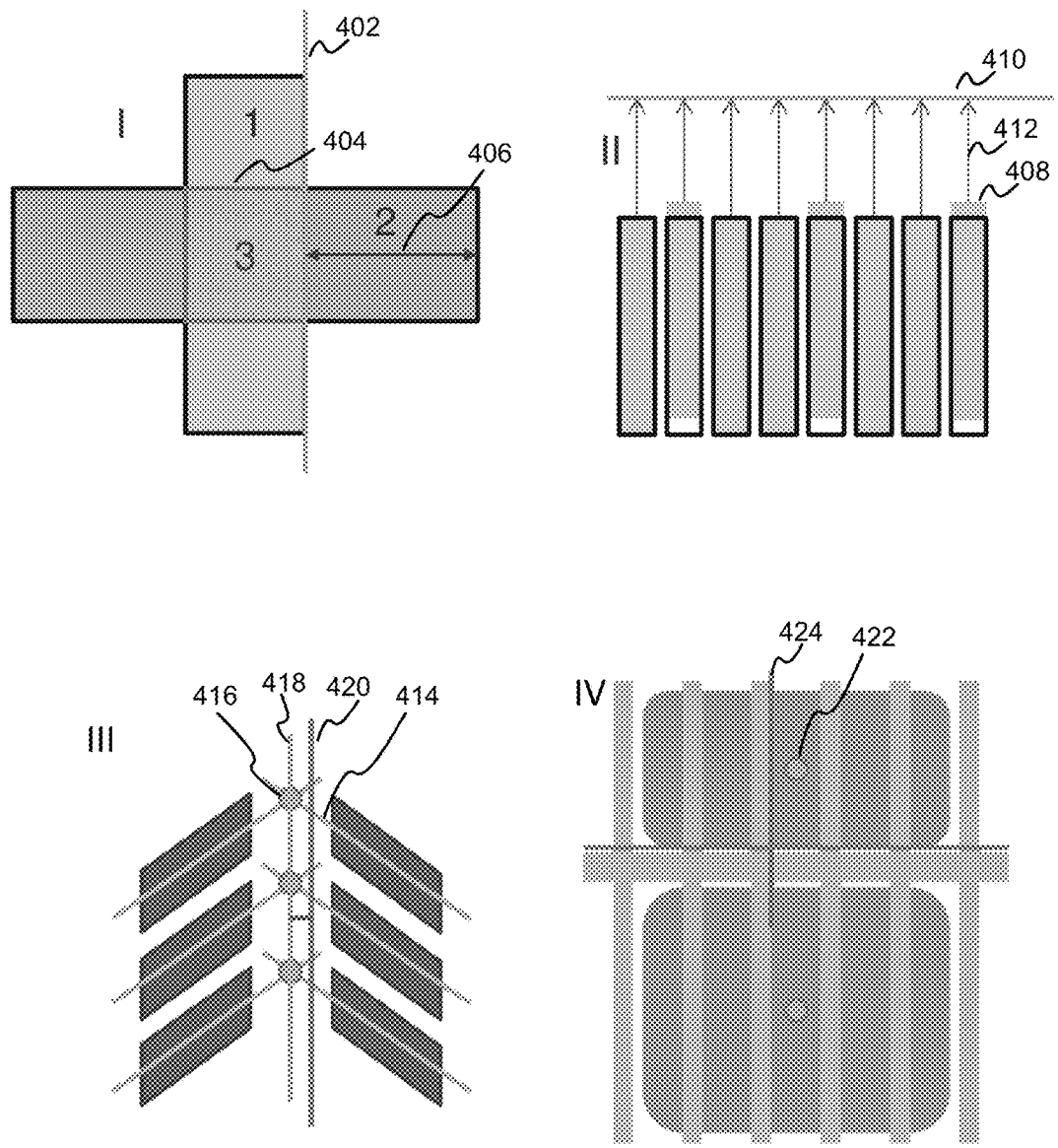
FIG. 4 illustrates examples of virtual objects in accordance with certain embodiments of the presently disclosed subject matter.

Turning now to FIG. 4, there are illustrated examples of virtual objects in accordance with certain embodiments of the presently disclosed subject matter. In graph I of FIG. 4, there are shown two intersected polygons which are originally present in a CAD clip: polygon 1 and polygon 2 as marked. A virtual object can be defined as a linear fit 402 to an edge (e.g., the right edge) of polygon 1. Another virtual object can be defined as the polygon 404 (i.e., the virtual rectangle 3 as marked) derived from the intersection of polygons 1 and 2. An operation of measurement, e.g., a distance 406 as shown in graph I can be defined with the assistance of the defined virtual objects. For instance, the distance 406 can be measured as a distance between the linear fit 402 and an edge of polygon 2. Alternatively, it can also be measured as a distance between the edge of polygon 404 and the edge of polygon 2. By way of another example, in graph II of FIG. 4, there are shown objects of rectangles 408 indicative of fins of a specimen. A virtual object can be defined as a virtual line 410 on design data, and an operation of measurement can be defined as a distance 412 between the upper edge of the rectangles 408 and the virtual line 410. As can be seen, graphs I and II illustrate virtual objects that are derived objects and are defined on design data.

By way of a further example, referring to graph III of FIG. 4, there are shown arrays of blobs on an inspection image. A virtual object can be defined as a major axis 414 identified for each blob. Another virtual object can be defined as an intersection point 416 of two adjacent major axes (resulted/derived from an operation of Finding intersection). A further virtual object can be a linear fit 418 resulted from an operation of Calculating linear fit of intersections on the inspection image. A similar virtual object can be defined as a linear fit 420 resulted from the same operation of Calculating linear fit of intersections but performed on the corresponding design data. A subsequent operation of calculating distance between the linear fit 418 and the linear fit 420 can result in a yet further virtual object of a distance (not shown in the graph). By way of yet a further example, graph IV shows another inspection image on which virtual objects of center point 422 (resulted from an operation of CoG) and linear fit 424 of an image object are defined. Further virtual objects can be defined as the corner of two linear fit as well as a distance between two objects of CoGs (not shown in the graph). As can be seen, graphs III and IV illustrate virtual objects that are derived objects and are defined on image data.

Accordingly, it can be arrived that derived objects can include structural elements that originally exist in a representation of the specimen (e.g., the objects resulted from a search operation), as well as virtual objects as defined above. Thus metrology objects can also be deemed as including structural elements and/or virtual objects. Metrology objects can also include ghost objects, as will be described in details below.

The process of objects being derived from operations and further operations being defined on the derived objects as described before can be repeated iteratively and such repetitive process is also referred to herein as "stack of operations".

In some embodiments, the definitions of one or more metrology operations can include where (i.e., on which representation) to perform the one or more metrology operations. This can be determined by one or more of the following factors: the type of the metrology operations, on which representation the metrology objects related to the metrology operations are defined and possibly one or more additional parameters defined by a user. By way of example, if a metrology object is defined as a polygon on a CAD clip, and the operation related to the object is Critical Dimension (CD), then the operation of CD can only be performed on the CAD clip, since the type of the operation CD determines that it will be performed at wherever the object is located. By way of another example, if a metrology object is defined as a structural element on the image, the operation related to the object is 'Distance from image to design', then this operation can be performed on both CAD and image, since the type of operation requires involvement of both CAD and image representation. By way of a further example, there may be such cases where based on the definition of the object and the type of operation related to the object, the operation should be performed on the image representation. However, there are provided more than one image representation as input, e.g., more than one inspection image are provided. In such cases, a user has the option to select among the inspection images and decide which image representation the operation will be performed on.

A representation group comprising a design-based representation of the specimen and an image-based representation of the specimen can also be accommodated (204) in the memory (e.g., either in the memory as comprised in the processing circuitry 102 or in the Storage unit 122 as illustrated in FIG. 1). The design-based representation of the specimen can be obtained, e.g., from the design data server 110, and can comprise design-based representation of at least a first metrology object of the one or more metrology objects. The image-based representation of the specimen can be captured, e.g., by the examination tool 114, using the examination recipe, and can comprise image-based representation of the at least first metrology object of the one or more metrology objects. In other words, the one or more metrology objects as defined can comprise at least one metrology object (i.e., the first metrology object) which has two corresponding representations: a design-based representation thereof on the design-based representation of the specimen (e.g., a CAD clip characterizing the specimen) and an image-based representation thereof on the image-based representation of the specimen (e.g., an inspection image of the specimen). The one or more metrology operations can include at least first metrology operation which is defined to be related to the at least first metrology object and to be performed on at least the image-based representation of the specimen.

According to certain embodiments, the design data used to define the one or more metrology objects and/or the one or more metrology operations can be the same as the design-based representation of the specimen to be measured or to be performed operations on. The one or more metrology operations can be defined related to at least one of the metrology objects. Accordingly, in such cases, each of the one or more metrology objects is defined either on the design-based representation of the specimen or on the image-based representation of the specimen.

In the cases where the one or more metrology objects are defined on the design-based representation of the specimen, the metrology operations, except for being defined as related to the metrology objects, can be further defined to be performed on the image-based representations of the specimen, or on both the image-based representations of the specimen and the design-based representation of the specimen. In the case that the one or more metrology objects are defined on the image-based representations of the specimen, the metrology operations, except for being defined as related to the metrology objects, can be further defined to be performed on the image-based representations of the specimen taking into consideration of the design-based representation of the specimen, or on both the image-based representations of the specimen and the design-based representation of the specimen.

According to some other embodiments, the design data used to define the one or more metrology objects and/or the one or more metrology operations is not necessarily the same as the design-based representation of the specimen to be measured or to be performed operations on. In one embodiment, the design data can be pre-acquired design data which is different from the design data of the specimen. For instance, the pre-acquired design data can be a representative design data or a reference design data provided for the purpose of defining the metrology objects and/or operations. Such pre-acquired design data may include different types (e.g., different shapes, sizes, etc.) of structural elements and/or patterns which, either individually or in appropriate combinations, can be used for defining the metrology objects. In such cases, the one or more metrology objects are defined on the pre-acquired design data, and at least one of the metrology operations is defined related to the one or more metrology objects.

It is to be noted that in such cases, since the design data of the specimen is different from the pre-acquired design data, it is possible that some of the defined metrology objects are not present in the design data of the specimen (for example, not present in a specific CAD clip). Therefore, a search on the design-based representation of the specimen can be performed in order to identify any metrology object of the defined one or more metrology objects that is present on the design-based representation of the specimen, i.e., the at least first metrology object of the one or more metrology objects as described above. For the identified objects resulted from the search, the operations defined as related to these objects are to be performed. For any metrology object that is defined in the pre-acquired design data but is not found in the design data of the specimen, the search result will return as null and thus no operations will be performed. One technical advantage of being able to define the metrology objects and/or operations on a pre-acquired design data is that, for a specific given metrology object, operations related thereto can be defined once and can be used with respect to different design data (e.g., CAD clips) of specimens, instead of defining the operations related to the same object each time when encountering such object in a different CAD clip. It is also to be noted that in this case some of the operations can be defined without relating to any objects, since when defining the operations, it is still unknown which metrology objects out of the defined objects may be present in the design data of the specimen. Therefore, an initial object such as a FOV object can be defined, and at least one operation can be defined related to the FOV object (e.g., a search operation). The subsequent operations can then be defined without reference to any specific object. For instance, a CD or a CoG operation can be defined to be performed on any object that may resulted from the search operation.

Similarly, in the above embodiments of defining the one or more metrology objects on a pre-acquired design data, the metrology operations can be defined to be performed on the image-based representations of the specimen, or on both the image-based representations of the specimen and the design-based representation of the specimen.

According to certain embodiments, the one or more metrology operations can be selected from a group comprising: Region of Interest (ROI) Operation, search operation, and measurement operation, etc. It is to be noted that although the operations of inspection/detection and segmentation are not explicitly listed here in the group, the output or results of these operations can be provided as initial objects for the metrology operations to be performed thereupon.

An operation of ROI can be defined as selecting a region or an area within the design data or image data for the purpose of performing subsequent operations. For instance, a ROI operation can result in a region within the FOV of a CAD clip for performing a subsequent search operation therein. The resulted region is sometimes also referred to as ROI. One example of a ROI can be a hotspot where, in view of design considerations, defects may occur at a higher probability thus require further inspection and measurement. Another example of a ROI can be a region informative of design layout of one or more different patterns of interest which can be specified or selected by a user or a design data processing unit.

A search operation is normally performed on design data and can be defined as searching for a specific object or an object of interest in a given region of the design data. By way of example, a search operation can be performed on an initial object, such as, e.g., the object of FOV as described above. By way of another example, a search operation can also be performed on the output of a preceding operation, such as, e.g., a ROI region resulted from ROI operation.

Figure 5:
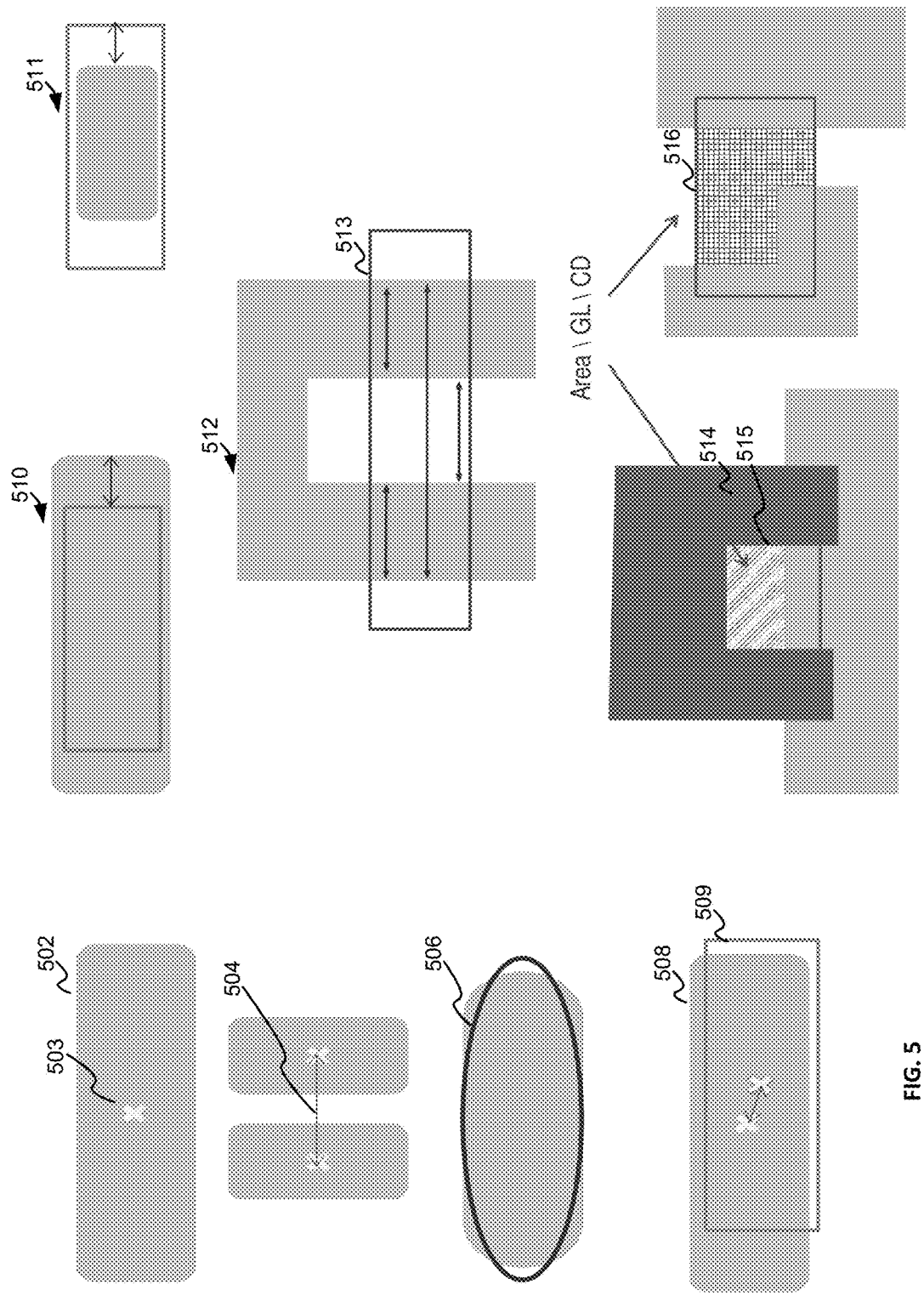
FIG. 5 illustrates examples of different types of measurement operations in accordance with certain embodiments of the presently disclosed subject matter.

A measurement operation should be expansively construed to cover any operation used to extract measurement information related to metrology objects. A measurement operation can be selected from a group comprising: Area of an object, Critical Dimension (CD)—length and width of dimensions of the object, Distance between objects, Center of Gravity (CoG) of an object, Gray Level (GL) statistics of an object, Contact Hole Analysis (CHA) of an object and additional shape-descriptors, 'Distance from image to design'—a comparison between design representation and image representation properties, and Arithmetic calculations, etc. Similarly, these terms can be used to refer to both the measurement operations and results of these operations. Turning now to FIG. 5, there are illustrated examples of different types of measurement operations in accordance with certain embodiments of the presently disclosed subject matter.

In one example, an operation of Center of Gravity (CoG) results in a point of CoG 502 which is the average location of the weight of an object 503. CoG refers the point at which weight of the object is evenly dispersed and all sides are in balance. The object 503 can be an object defined on the design data or on the image data. In another example, an operation of Distance between two CoGs is illustrated which results in the object of distance 504. In a further example, an operation of Contact Hole Analysis (CHA) can provide an output of an ellipse 506 that fit in the object in the shape of a polygon. In yet a further example, an operation of 'Distance from image to design' is exemplified as a distance between a CoG of an image-based representation 508 of an object and a CoG of a corresponding design-based representation 509 of the same object. The design-based representation 509 of the object is mapped with the corresponding image-based representation 508 and both representations are shown together in relative positions for the purpose of measuring the distance. The mapping process will be described in details below with reference to FIG. 3. Another example of 'Distance from image to design' is illustrated in 510 and 511 where a distance between an edge of a design object and an edge of a corresponding image object can be measured (namely, in 510 the design object falls within the image object and in 511 it is illustrated the other way around). In 512 there are illustrated operations of Critical Dimension (CD) related to a N-shaped polygon. CD refers to distances between borders or edges of an object or objects. As shown in 512, a ROI 513 is defined and four CDs are measured within the ROI 513. In yet a further example, within a ROI 514, a background area 515 formed by two surrounding polygons is illustrated, for which an operation of Area (which results in the size of the area) and an operation of Gray Level (GL) (which results in the value of the grayscale level of the area) can be performed. Within a ROI 516, a list of CDs (e.g., distances between edges of two polygons) can be measured. Operations of Arithmetic calculation (not illustrated in FIG. 5) can take one or more results of the measurement operations as inputs for performing arithmetic calculations thereupon (e.g., addition, subtraction, etc).

It is to be noted that the measurements shown in FIG. 5 are illustrated as non-limiting examples and are for the purpose of illustration only and should by no means be construed as limiting the present disclosure in any way. Other measurements or other examples of the above described measurements can be defined and performed in addition to or in lieu of the above.

Figure 3:
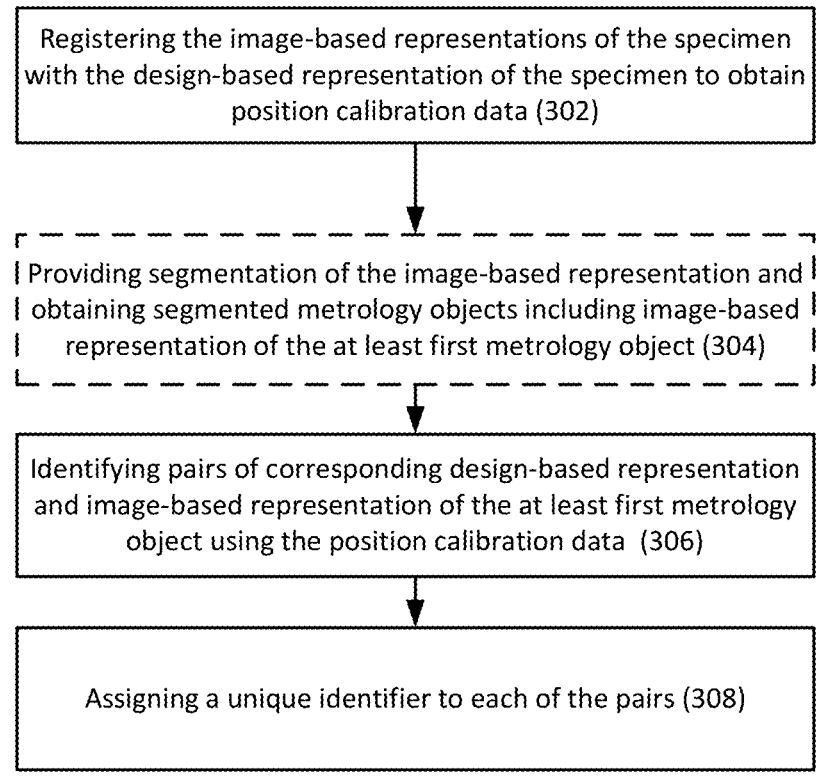
FIG. 3 illustrates a generalized flow chart of a mapping process in accordance with certain embodiments of the presently disclosed subject matter.

Continuing the process in FIG. 2, once the examination recipe is generated specifying the metrology objects and metrology operations related to a metrology application, and design-based representation and image-based representation of the specimen are obtained, a mapping between the design-based representation of the at least first metrology object and the image-based representation of the at least first metrology object can be performed (206) (e.g., by the mapping module 106 illustrated in FIG. 1). Turning now to FIG. 3, there is provided a generalized flow chart of a mapping process in accordance with certain embodiments of the presently disclosed subject matter.

The image-based representations of the specimen can be registered (302) with the design-based representation of the specimen to obtain position calibration data. The mapping module 106 registers the image-based representations of the specimen (e.g., an inspection image) with regard to the corresponding design-based representation of the specimen (e.g., a CAD clip) thereby obtaining for the inspection image (or part thereof, e.g., ROI, or pattern of interest) coordinates in design space (coordinates in design space are referred to as design coordinates). Some differences between the coordinates of the inspection image and the corresponding locations in design coordinates are likely to occur for various reasons—scanning conditions (e.g. illumination) as well as imperfections, shifts and outright errors in the scanning process, errors in the manufacturing of the electric circuit printed on the wafer, and so forth.

The mapping module 106 further generates position calibration data. The position calibration data can be informative of a global (e.g. average) offset between the inspection image and design data and/or of multiple offsets, each related to a specific region or pattern or object of interest thereof. Optionally, the position calibration data can comprise a data structure specifying respective offsets for each object of interest (or groups thereof). The position calibration data can be stored in the memory as comprised in the processing circuitry 102 or the storage unit 122. The registration and position calibration generation process can be implemented according to any suitable method of registration algorithms known in the art (e.g. as described in US2007/0280527, US2013/204569 etc).

In cases where the at least first metrology objects is defined in design data, upon obtaining the image-based representation (e.g., the inspection image) of the specimen, the mapping module 106 further segments (304) the inspection image into groups of pixels belonging to the same object (or provides segmentation information of the inspection image), thereby identifying continuous regions corresponding to different metrology objects. Segmentation is provided to the inspection image or part thereof (e.g., the image area corresponding to the FOV or ROI) and is referred to as a global segmentation. The segmentation process can be implemented according to one or more similarity and/or discontinuity criteria and segmentation algorithm(s) known in the art, including, by way of example, histogram-based, edge-based, boundary-based, watershed and/or other segmentation algorithms. Through the segmentation, segmented metrology objects can be obtained (304) including the image-based representation of the at least first metrology object. Segmented metrology objects revealed by the segmentation can be stored in the memory as comprised in the processing circuitry 102 or in the storage unit 122. It is to be noted the step of segmentation is optional in some cases. For instance, if the metrology objects are originally defined on an inspection image, e.g., provided by an operation of segmentation or revealed by an inspection process, the step of segmentation can be omitted.

Pairs of corresponding design-based representation and image-based representation of the at least first metrology object can be identified (306) using the position calibration data and a unique identifier can be assigned (308) to each corresponding pair. By way of example, each design metrology object can be assigned with a unique identifier. For each given segmented metrology object, design coordinates of the inspection image (or part thereof) can be used for identifying a design metrology object corresponding to the segmented metrology object. Once identified, each segmented metrology object and pixels thereof can be assigned with the same unique identifier as of corresponding design metrology object. Alternatively, the identification process can start with assigning the unique identifier to a segmented metrology object, then using the position calibration data to identify a corresponding design metrology object which will then be assigned to the same unique identifier. An exemplified segmentation and mapping process is described in U.S. patent application Ser. No. 14/727,800 published on Dec. 1, 2016, which is incorporated herein in its entirety by reference.

It is to be noted that, except for the at least first metrology object that has both design and image representations, there may be certain metrology objects among the one or more metrology objects as defined which only have one representation (i.e., objects that only have design representation or image representation). For such objects, there may not be found any corresponding image or design representation thereof through the above mapping process. Therefore a different process is needed for performing operations related to these objects, as will be detailed below.

According to certain embodiments, the one or more metrology objects can include at least one metrology object (also referred to as at least a second metrology object, to be distinguished from other objects defined herein) which has only a design-based representation thereof on the design-based representation of the specimen (i.e., does not have image-based representation thereof). For instance, due to causes such as, e.g., manufacture error or scanning conditions etc., certain metrology objects that are present in the design data of a specimen may be absent in the corresponding image data of the specimen. Such objects that only have design representation are sometimes referred to as "ghost objects". At least one metrology operation of the one or more metrology operations (also referred to as at least a second metrology operation, to be distinguished from other operations defined herein) is defined as related to the at least second metrology object and to be performed on the image-based representation or on both the design-based representation of the specimen and the image-based representation.

For these objects, similarly as described with reference to block 302, the image-based representations of the specimen can be registered with the design-based representation of the specimen to obtain position calibration data. A position indication of the at least second metrology object on the image-based representation of the specimen can then be identified using the position calibration data. By way of example, the offset between the inspection image and design data can be used to find a relative position of the at least second metrology object on the inspection image as compared to the design representation thereof. The at least second metrology operation of the one or more metrology operations related to the at least second metrology object can be performed according to definition of the at least second metrology operation using the position indication. As aforementioned, the definition of the at least second metrology operation can determine that the at least second metrology operation can be performed on the image representation or on both image and design representation.

According to certain embodiments, the one or more metrology objects can include at least one defect object that has only an image-based representation thereof on the image-based representation of the specimen. For a defect object, since it is produced due to certain manufacture error in the manufacture process of the specimen, there is no corresponding design-based representation thereof on the original design data of the specimen. Metrology operations related to a defect object can be defined with reference to design data of the specimen.

In some further cases, at least one metrology operation of the one or more metrology operations (also referred to as at least a third metrology operation, to be distinguished from other operations defined herein) can be defined as related to the at least one defect object and to be performed on both the image-based representation and the design-based representation of the specimen. In such cases, similarly as described with reference to block 302, the image-based representations of the specimen can be registered with the design-based representation of the specimen to obtain position calibration data. A position indication of the at least one defect object on the design-based representation of the specimen can be identified using the position calibration data. By way of example, the offset between the inspection image and design data can be used to find a relative position of the at least one defect object on the design representation of the specimen as compared to the position of the at least one defect object on the image representation of the specimen. By way of another example, in cases where one or more neighboring metrology objects are present in the vicinity of the defect object on the image-based representation of the specimen which have corresponding design-based representation thereof on the design-based representation of the specimen, such neighboring metrology objects can be identified and mapped with the corresponding design-based representation thereof using position calibration data. A position indication of the at least one defect object on the design-based representation of the specimen can be identified using the design-based representation of the neighboring metrology objects as an anchor. The at least third metrology operation can then be performed on both the image-based representation and the design-based representation of the specimen using the position indication.

Figure 6:
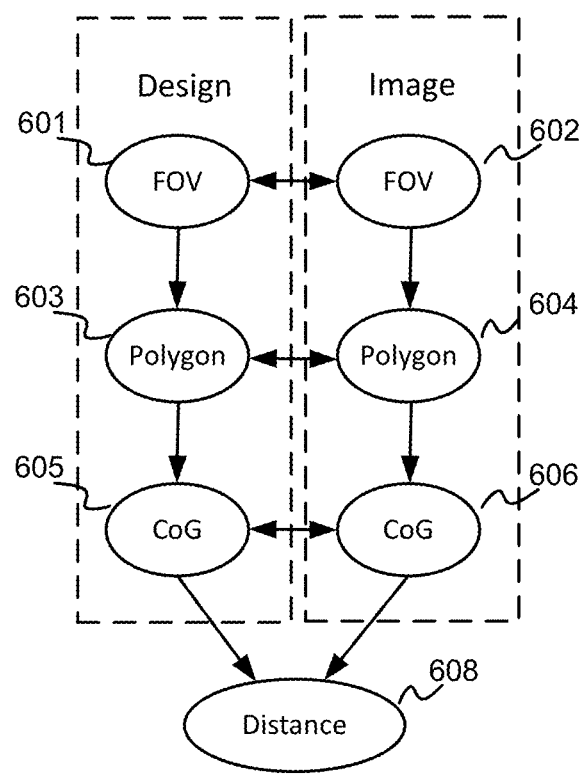
FIG. 6 illustrates an example of metrology objects associated with the attribute of context in accordance with certain embodiments of the presently disclosed subject matter.

According to certain embodiments, at least one of the metrology objects as defined can be associated with an attribute of context indicative of a parent object thereof. Turning now to FIG. 6, there is illustrated an example of metrology objects associated with the attribute of context in accordance with certain embodiments of the presently disclosed subject matter.

As shown, there are illustrated pairs of corresponding design representation and image representation of metrology objects (i.e., corresponding design objects and image objects) and sequence of operations related thereto. A design object of FOV 601 is defined on the design data of the specimen. A polygon 603 is identified within FOV 601 (e.g., through a search operation), and an object of CoG 605 can be resulted from an operation of CoG performed on the polygon 603. Similarly, on the corresponding image representation of the specimen, image objects of FOV 602, polygon 604 and CoG 606 are also defined which respectively correspond to FOV 601, polygon 603 and CoG 605. An object of Distance 608 between two CoGs 606 and 608 can be resulted from performing an operation of 'Distance from image to design' on the two CoGs. By way of example, the object of Distance 608 can have an attribute of context associated therewith indicating that Distance 608 is related to polygons 603 and 604 (e.g., polygons 603 and 604 are parents objects of Distance 608). The attribute of context can be identified through sequence of operations. The parents objects associated therewith can include direct parent objects and/or indirect parent objects. For a given object, with which parent objects to associate as context can depend on the type of the object. In some cases, a given object may not have a parent object thereof (e.g., the object of FOV). In that case, the context of the given object can be itself. In some embodiments, the attribute of context can form part of the definition of the metrology objects and can be used to report result of the metrology operations from which the metrology objects are derived.

Referring back to the process of FIG. 2, the at least first metrology operation of the one or more metrology operations related to the at least first metrology object can be performed (208) (e.g., by the Operation performing module 108 illustrated in FIG. 1) according to the examination recipe using the mapping. The at least first metrology operation is defined/specified in the examination recipe as related to the at least first metrology object and to be performed on at least the image-based representation of the specimen. In some embodiments, the definition of the at least first metrology operation in the examination recipe can also include where (e.g., which representation(s)) to perform such operation, which is determined by one or more of the following factors: the type of the metrology operations, a representation where the metrology objects related to the metrology operations are defined and one or more additional parameters defined by a user, as described above. Therefore, when performing the at least first metrology operation, the Operation performing module 108 can obtain the information of where to perform the operation from the definition of the operation, and perform the operation on the representation(s) as defined. By way of example, when the metrology objects are defined on the design-based representation of the specimen, the metrology operations related thereto are defined to be performed on the image-based representations of the specimen, or on both the image-based representations of the specimen and the design-based representation of the specimen. When the one or more metrology objects are defined on the image-based representations of the specimen, the metrology operations are defined to be performed on both the image-based representations of the specimen and the design-based representation of the specimen. Thus the mapping process as described above with reference to FIG. 3 is needed when performing the metrology operations since the definition of metrology object and the performing of the metrology operations together require both representations of the metrology objects.

Referring back to the system of FIG. 1, as aforementioned, using GUI 124, a user may select metrology objects and metrology operations related to a metrology application, to thereby generate an examination recipe (i.e., recipe setup or generation). During recipe set up, in order to verify the examination recipe, the examination tool may capture one or more test image-based representations of the specimen using the examination recipe. The metrology tool 100 may perform measurements in accordance with the defined metrology objects and metrology operations, and a decision to accept or refine the definition of such metrology objects and metrology operations based on respective measurement results can be received by a user or in an automated manner Once an examination recipe is verified and generated, the examination tool 114 and the metrology tool 100 may implement the examination recipe and performs measurements on a plurality of specimens in accordance with the examination recipe (i.e., run time measurement), as will be described in detail below with reference to FIG. 7. The metrology results may be presented via GUI 124.

Figure 7:
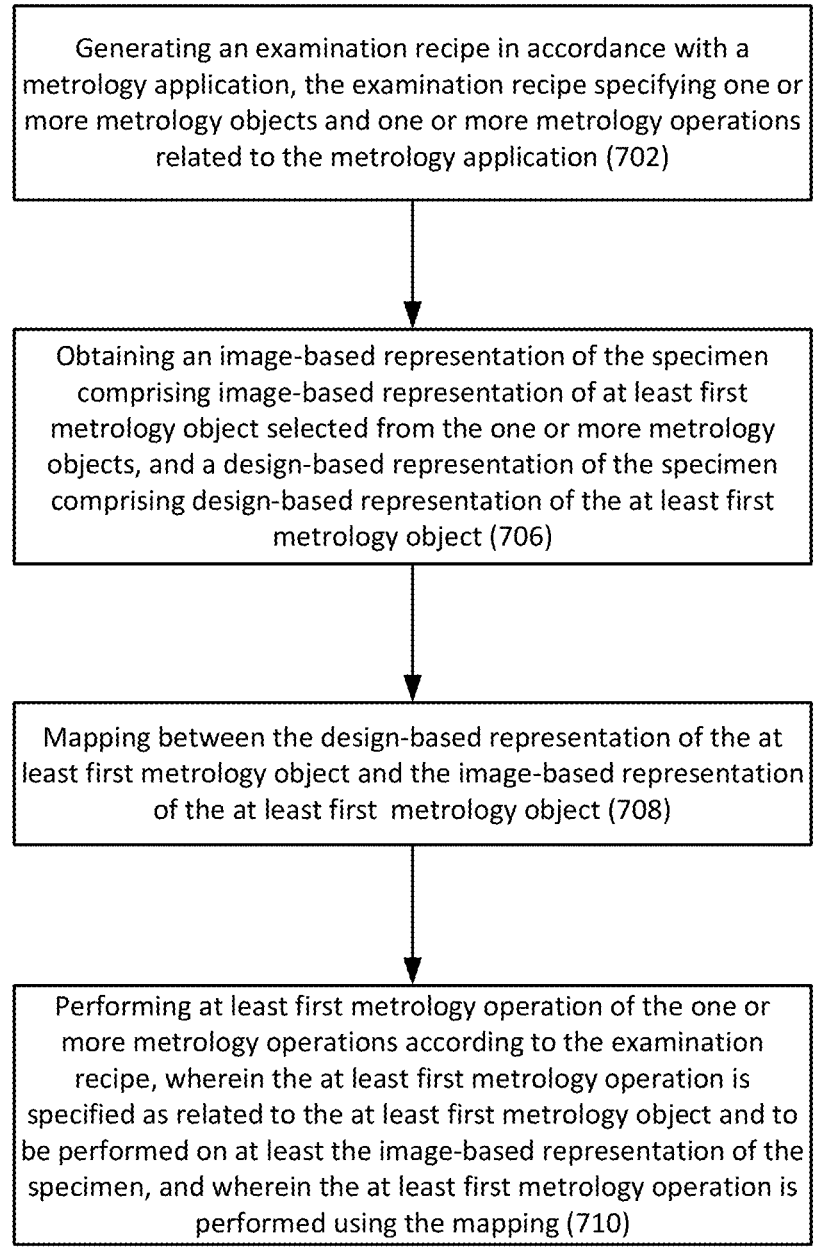
FIG. 7 illustrates a generalized flow chart of performing metrology operations related to a specimen by an examination system in accordance with certain embodiments of the presently disclosed subject matter.

Turning now to FIG. 7, there is illustrated a generalized flow chart of performing metrology operations related to a specimen by an examination system in accordance with certain embodiments of the presently disclosed subject matter.

During recipe setup phase, an examination recipe can be generated (702) (e.g., by a computer-based recipe unit 112) in accordance with a metrology application. The examination recipe can specify/define one or more metrology objects and one or more metrology operations related to the metrology application. At least one of the group consisting of the one or more metrology objects and the one or more metrology operations is specified/defined with reference to design data. In other words, the one or more metrology objects and/or the one or more metrology operations can be specified with reference to design data. The metrology application can be selected from a group comprising: Measurement-Based Inspection (MBI), Critical Dimension Uniformity (CDU), 3-Dimentional Uniformity (3DU), CAD Awareness (CADA) and Overlay (OVL). Details related to metrology application, metrology objects and metrology operations are described above with reference to FIGS. 1 and 2, and will not be repeated here for brevity and simplicity of the specification.

Optionally, the recipe setup phase can further comprise a recipe verification phase, in which the examination recipe can be used to capture one or more test image-based representations of the specimen, and the mapping and the performing as described with reference to block 708 and block 710 can be performed with respect to the test image-based representations to verify the examination recipe. The examination recipe (e.g., the definition of such metrology objects and/or metrology operations) can be accepted or refined based on respective measurement results from performing the metrology operations on the test image data.

Once the examination recipe is verified and/or refined, it can be used in runtime measurement, i.e., one or more specimens can be measured in accordance with the examination recipe.

An image-based representation of the specimen and a design-based representation of the specimen can be obtained (706) (e.g., by the processing circuitry 102 via the I/O interface 120). Specifically, during runtime phase, the examination recipe can be used (e.g., by an examination tool 114) to capture the image-based representation of the specimen. The image-based representation of the specimen can comprise image-based representation of at least first metrology object selected from the one or more metrology objects. Details related to examination, examination recipe and examination tools are described above with reference to FIGS. 1 and 2, and will not be repeated here.

The design-based representation of the specimen can be obtained, e.g., from a design data server. The design-based representation of the specimen comprises design-based representation of the at least first metrology object. In other words, there exists at least one metrology object, i.e., the at least first metrology object, which has two corresponding representations on both design and image representation of the specimen.

The design-based representation of the at least first metrology object and the image-based representation of the at least first metrology object can be mapped (708) (e.g., by the mapping module 106 as comprised in the processing circuitry 102). The mapping is performed in a similar manner as described above with reference to block 206 as well as FIG. 3.

At least first metrology operation of the one or more metrology operations can be performed (710) (e.g., by the operation performing module 108 as comprised in the processing circuitry 102) according to the examination recipe. The at least first metrology operation is specified/defined as related to the at least first metrology object and to be performed on at least the image-based representation of the specimen. The at least first metrology operation is performed using the mapping as described in block 708. The performing metrology operation(s) is implemented in a similar manner as described above with reference to block 208.

It is to be noted that the examples and embodiments described herein are illustrated as non-limiting examples and should not be construed to limit the presently disclosed subject matter in any way.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, implemented on a suitably programmed computer. Likewise, the invention contemplates a computer program being readable by a computer for executing the method of the invention. The invention further contemplates a non-transitory computer-readable storage medium tangibly embodying a program of instructions executable by the computer for executing the method of the invention.

Those skilled in the art will readily appreciate that various modifications and changes can be applied to the embodiments of the invention as hereinbefore described without departing from its scope, defined in and by the appended claims.

The invention claimed is:

1. An examination system capable of performing metrology operations related to a specimen, comprising:
    a computer-based recipe unit configured to generate an examination recipe in accordance with a metrology application, the examination recipe specifying one or more metrology objects and one or more metrology operations related to the metrology application, wherein at least one of the group consisting of the one or more metrology objects and the one or more metrology operations is specified with reference to design data; and
    a metrology tool comprising a processing circuitry, wherein the metrology tool is configured to:
        obtain an image-based representation of the specimen comprising image-based representation of at least first metrology object selected from the one or more metrology objects, and a design-based representation of the specimen comprising design-based representation of the at least first metrology object;
        map between the design-based representation of the at least first metrology object and the image-based representation of the at least first metrology object; and
        perform at least a first metrology operation of the one or more metrology operations according to the examination recipe, wherein the at least first metrology operation is specified in the examination recipe as related to the at least first metrology object and to be performed on at least the image-based representation of the specimen, and wherein the at least first metrology operation is performed using the mapping.

2. The examination system of claim 1, further comprising an examination tool configured to use the examination recipe to capture the image-based representation of the specimen.

3. The examination system of claim 1, wherein the recipe unit is implemented as part of the metrology tool.

4. The examination system of claim 1, wherein the metrology application is selected from a group comprising: Measurement-Based Inspection (MBI), Critical Dimension Uniformity (CDU), 3-Dimentional Uniformity (3DU), CAD Awareness (CADA) and Overlay (OVL).

5. The examination system of claim 1, further comprising a graphical user interface (GUI) configured to enable a user to select the metrology application from one or more metrology applications and the at least first metrology object related to the metrology application.

6. The examination system of claim 2, wherein the examination tool is further configured to capture one or more test image-based representations of the specimen using the examination recipe, and wherein the mapping and the performing are performed with respect to the test image-based representations to verify the examination recipe.

7. The examination system of claim 2, wherein the examination recipe comprises one or more illumination conditions to be used by the examination tool for capturing the image-based representation of the specimen, the one or more illumination conditions derived with respect to the metrology application and the specimen.

8. The examination system of claim 1, wherein each of the one or more metrology objects is selected from a group comprising: a structural element, a virtual object, and a ghost object, wherein the virtual object is a metrology object that does not have an original design-based representation thereof, and the ghost object is a metrology object that only has design-based representation thereof.

9. The examination system of claim 1, wherein the metrology tool is configured to map between the design-based representation and the image-based representation of the at least first metrology object by registering the image-based representation of the specimen with the design-based representation of the specimen to obtain position calibration data, identifying at least a pair of corresponding design-based representation and image-based representation of the at least first metrology object using the position calibration data and assigning a unique identifier to each of the at least a pair.

10. The examination system of claim 1, wherein the one or more metrology objects are specified on the design-based representation of the specimen and the one or more metrology operations are specified to be performed on the image-based representation of the specimen, or on both the image-based representation of the specimen and the design-based representation of the specimen.

11. The examination system of claim 1, wherein the one or more metrology objects are specified on the image-based representation of the specimen and the one or more metrology operations are specified to be performed on both the image-based representation of the specimen and the design-based representation of the specimen.

12. The examination system of claim 1, wherein the design data is a pre-acquired library of design data, the one or more metrology objects are defined in the pre-acquired library of design data, and at least one of the metrology operations is defined related to the one or more metrology objects, and wherein the metrology tool is further configured to:
search on the design-based representation of the specimen to identify the at least first metrology object.

13. The examination system of claim 1, wherein the one or more metrology objects comprise at least a second metrology object having only a design-based representation thereof on the design-based representation of the specimen, and at least a second metrology operation of the one or more metrology operations is specified to be related to the at least second metrology object and to be performed on the image-based representation or on both the design-based representation and the image-based representation of the specimen, and wherein the metrology tool is further configured to:
register the design-based representation of the specimen and the image-based representation of the specimen to obtain position calibration data;
identify a position indication of the at least second metrology object on the image-based representation of the specimen using the position calibration data; and
perform the at least second metrology operation according to definition of the at least second metrology operation in the examination recipe using the position indication.

14. The examination system of claim 1, wherein the one or more metrology objects comprise at least one defect object having only an image-based representation thereof on the image-based representation of the specimen, and at least a third metrology operation of the one or more metrology operations is specified to be related to the at least one defect object and to be performed on both the image-based representation and the design-based representation of the specimen, and wherein the metrology tool is further configured to:
register the design-based representation of the specimen and the image-based representation of the specimen to obtain position calibration data;
identify a position indication of the at least one defect object on the design-based representation of the specimen using the position calibration data; and
perform the at least third metrology operation on both the image-based representation and the design-based representation of the specimen according to definition of the at least second metrology operation in the examination recipe using the position indication.

15. A computerized method of performing metrology operations related to a specimen, comprising:

generating, by a computer-based recipe unit, an examination recipe in accordance with a metrology application, the examination recipe specifying one or more metrology objects and one or more metrology operations related to the metrology application, wherein at least one of the group consisting of the one or more metrology objects and the one or more metrology operations is specified with reference to design data;
obtaining, by a metrology tool, an image-based representation of the specimen comprising image-based representation of at least a first metrology object selected from the one or more metrology objects, and a design-based representation of the specimen comprising design-based representation of the at least first metrology object;
mapping, by the metrology tool, between the design-based representation of the at least first metrology object and the image-based representation of the at least first metrology object; and
performing, by the metrology tool, at least a first metrology operation of the one or more metrology operations according to the examination recipe, wherein the at least first metrology operation is specified as related to the at least first metrology object and to be performed on at least the image-based representation of the specimen, and wherein the at least first metrology operation is performed using the mapping.

16. The computerized method of claim 15, wherein the metrology application is selected from a group comprising: Measurement-Based Inspection (MBI), Critical Dimension Uniformity (CDU), 3-Dimentional Uniformity (3DU), CAD Awareness (CADA) and Overlay (OVL).

17. The computerized method of claim 15, further comprising using, by an examination tool, the examination recipe to capture the image-based representation of the specimen.

18. A recipe unit, comprising:
a graphical user interface (GUI) configured to define a metrology application, and define one or more metrology objects and one or more metrology operations related to the metrology application, wherein at least one of the group consisting of the one or more metrology objects and the one or more metrology operations is defined with reference to design data, and wherein the one or more metrology objects comprise at least one of a virtual object and a ghost object, wherein the virtual object is a metrology object that does not have an original design-based representation thereof, and the ghost object is a metrology object that only has design-based representation thereof; and
a processing circuitry operatively connected to the GUI, the processing circuitry comprising a memory and a processor operatively coupled thereto and configured to generate an examination recipe in accordance with definitions of the metrology application, the one or more metrology objects and one or more metrology operations.

19. The recipe unit of claim 18, wherein the one or more metrology objects comprise a ghost object, and at least one metrology operation of the one or more metrology operations is defined to be related to the ghost object and to be performed on the image-based representation or on both the design-based representation of the specimen and the image-based representation.

20. The recipe unit of claim 18, wherein the one or more metrology objects comprise a virtual object which is a defect object having only an image-based representation thereof on the image-based representation of the specimen, and at least one metrology operation of the one or more metrology operations is defined to be related to the defect object and to be performed on both the image-based representation and the design-based representation of the specimen.

* * * * *